United States Patent [19]

Redpath et al.

[11] Patent Number: 4,952,571
[45] Date of Patent: Aug. 28, 1990

[54] PYRIDAZINONE DERIVATIVES

[75] Inventors: James Redpath, Bishopbriggs; Robert T. Logan, Lanark; Robert G. Roy, Larkhall; George McGarry, Airdrie, all of Scotland

[73] Assignee: Akzo, N.V., Arnhem, Netherlands

[21] Appl. No.: 378,342

[22] Filed: Jul. 11, 1989

[30] Foreign Application Priority Data

Jul. 11, 1988 [EP] European Pat. Off. ....... 88.306295.2

[51] Int. Cl.$^5$ ..................... A61K 31/50; C07D 237/06
[52] U.S. Cl. ................. 514/254; 514/233.5; 544/146; 544/238; 544/153
[58] Field of Search ...................... 544/238, 146, 153; 514/254, 233.5

[56] References Cited

U.S. PATENT DOCUMENTS

| | | | |
|---|---|---|---|
| 4,225,711 | 9/1980 | Steinman | 544/238 |
| 4,647,564 | 3/1987 | Robertson | 544/238 |
| 4,870,077 | 9/1989 | Von Dersaal | 544/238 |

Primary Examiner—Donald G. Daus
Attorney, Agent, or Firm—William M. Blackstone

[57] ABSTRACT

The invention relates to pyridazinone compounds of the general formula I:

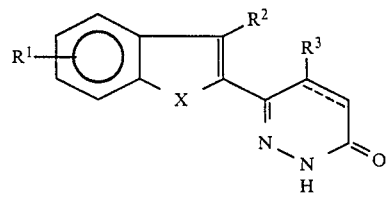

wherein
$R^1$ represents one to four substituents, which may be the same or different and are selected from H, OH, halogen, $NO_2$, unsubstituted or C1-C4 alkyl substituted amino, C1-C4 alkyl, C1-C4 halogen substituted alkyl, O—ALK—$NR^4R^5$, C1-C4 alkoxy, whereby two substituents taken together may also represent a methylenedioxy group;
$R^2$ and $R^3$ represent independently H or C1-C4 alkyl;
$R^4$ and $R^5$ represent independently H or C1-C4 alkyl, or form together with the nitrogen a 5- or 6- membered ring;
X represents S or O;
the dotted line represents an optional bond;
and their pharmaceutically acceptable salts.

The compounds according to the invention have a cardiotonic, blood platelet aggregation inhibiting, systemic vasodilator, pulmonary vasodilator, and bronchodilator activity, and more particularly they show a very potent increase of the force of the muscular contractions of the heart, reduce afterload on the heart, improve pulmonary blood flow, and improve airways ventilation.

6 Claims, No Drawings

PYRIDAZINONE DERIVATIVES

The invention relates to pyridazinone compounds of the general formula I:

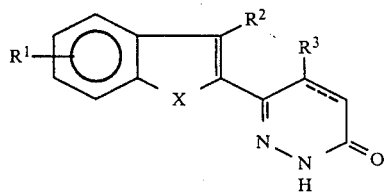

wherein
$R^1$ represents one to four substituents, which may be the same or different and are selected from H, OH, halogen, $NO_2$, unsubstituted or C1–C4 alkyl substituted amino, C1–C4 alkyl, C1–C4 halogen substituted alkyl, O-ALK-$NR^4R^5$, C1–C4 alkoxy, whereby two substituents taken together may also represent a methylenedioxy group;
$R^2$ and $R^3$ represent independently H or C1–C4 alkyl;
$R^4$ and $R^5$ represent independently H or C1–C4 alkyl, or form together with the nitrogen a 5- or 6-membered ring,
X represents S or O;
the dotted line represents an optional bond;
and their pharmaceutically acceptable salts.

The compounds according to the invention have a cardiotonic, blood platelet aggregation inhibiting, systemic vasodilator, pulmonary vasodilator, and bronchodilator activity, and more particularly they show a very potent increase of the force of the muscular contractions of the heart, reduce afterload on the heart, improve pulmonary blood flow, and improve airways ventilation, which may be mediated by phosphodiesterase inhibition, and among others can be used for treating heart failure and asthma.

Preferred compounds have 2, 3 or 4 substituents $R^1$, selected from OH, halogen, C1–C4 alkoxy or O-ALK-$NR^4R^5$, and $R^2$ and $R^3$ represent H or $CH_3$.

Especially mentioned are compounds wherein $R^1$ represents 2 or 3 substituents selected from OH, F, Cl, Br, $OCH_3$, $OC_2H_5$, 2-(piperidin-1-yl)ethyloxy or 2-(piperidin-1-yl)propyloxy, $R^2$ represents H, $R^3$ represents $CH_3$, X represents S, and the optional bond is not present, and in particular compound II

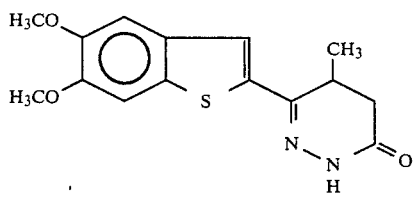

By the term C1–C4 alkyl, used in the definition of $R^1$, is meant a saturated hydrocarbon with 1 to 4 carbon atoms, such as methyl, ethyl, propyl, isopropyl, butyl, isobutyl, sec-butyl and tert-butyl.

With the term C1–C4 alkoxy is meant an alkoxy group, in which the term alkyl has a similar meaning as above.

By halogen is preferably meant fluorine, chlorine and bromine.

With the term ALK is meant a branched or unbranched alkylene group with 2–6 C atoms, and preferably 2–4 C atoms, which optionally may be substituted with hydroxy or halogen.

The 5- and 6-ring formed by $R^4$ and $R^5$ together with the nitrogen atom, may have an additional oxygen or nitrogen atom, may be saturated or unsaturated, and may substituted with C1–C4 alkyl. Examples of O-ALK-$NR^4R^5$ groups are 2-aminoethyloxy, 3-(methylamino)-propyloxy, 2-(dimethylamino)-ethyloxy, 2-(piperidin-1-yl)ethyloxy, 3-(piperidin-1-yl)propyloxy, 2-(piperazin-1-yl)ethyloxy, 2-(4-methylpiperazin-1-yl)ethyloxy, 3-(morpholin-1-yl)-propyloxy, 2-methyl-3-(piperidin-1-yl)propyloxy, 2-hydroxy-3-(piperidin-1-yl)propyloxy, 2-(imidazol-1-yl)-ethyloxy, and the like.

Pharmaceutically acceptable salts are acid addition salts derived from acids, such as hydrochloric acid, sulphuric acid, phosphoric acid, acetic acid, propionic acid, glycolic acid, maleic acid, fumaric acid, malonic acid, succinic acid, tartaric acid, lactic acid, citric acid, ascorbic acid, salicylic acid, benzoic acid and methanesulphonic acid, and the like.

The compounds of this invention may be prepared by any method known for the preparation of analogous compounds.

A suitable method of preparation of compounds according to general formula I is condensation of a ketoacid of formula III

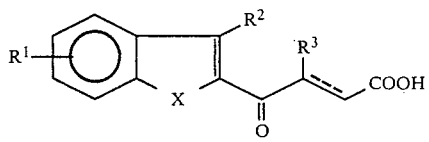

wherein $R^1$, $R^2$, $R^3$, X and the dotted line have the aforesaid meanings or its alkyl (C1–C8) ester or carboxylic acid salt thereof with hydrazine, and preferably with hydrazine hydrate.

This condensation is preferably performed in a suitable solvent like dioxan, ethanol, methanol, dimethylformamide and the like, or mixtures thereof. The reaction temperature is preferably between room temperature and reflux temperature of the solvent used.

The product obtained in the above mentioned process is subsequently oxidized if the dotted line of formula I represents a bond, and this bond is not present in keto acid III.

Oxidation may be performed by standard procedures. Well-known oxidation reagents include DDQ, $CrO_3$, $KMnO_4$, $MnO_2$ or air in the presence of a suitable catalyst like Pt or Pd, and the like.

The carboxylic acid salt of a compound of formula III is derived from a base, preferably comprising an alkali or earth-alkali metal, including Na, K, Ca and Mg. The term alkyl (C1–C8) ester, represents esters derived from an aliphatic alkylalcohol with 1 to 8 carbon atoms, of which the alkyl group may be methyl, ethyl, propyl, butyl, sec-butyl, octyl, and the like.

Keto acid III can be prepared by various routes, known for the preparation of analogous compounds. For the preparation of keto acid III reference is made to the flow sheet and the actual examples.

Compounds of general formula I may be converted into other compounds of general formula I. For instance, some substituents $R^1$ can easily be cleaved, after which the compound obtained may be used as such or brought into reaction with suitable reagents according to methods known per se. If $R^1$, for instance, represents an alkoxy group, this group may be cleaved by known methods, e.g. by strong Lewis acids like boron tribromide, to give compounds according to this invention with $R^1$ is hydroxy. Compounds of the general formula I with $R^1$ is hydroxy may be converted into compounds with $R^1$ is alkoxy or $NR^4R^5$ substituted alkoxy, e.g. by reaction with an $NR^4R^5$ substituted or unsubstituted alkyl group, which is provided with a suitable leaving group, such as the p-toluenesulphonate group or a halogen.

This method is particularly useful for the preparation of compounds of general formula I wherein $R^1$ is O-ALK-$NR^4R^5$.

The compounds of formula I may -if appropriate- be isolated from the reaction mixture in the form of a pharmaceutically acceptable salt. The pharmaceutically acceptable salts may also be obtained by treating the free base of formula I with an organic or inorganic acid such as HCl, HBr, HI, $H_2SO_4$, $H_3PO_4$, acetic acid, propionic acid, glycolic acid, maleic acid, malonic acid, succinic acid, tartaric acid, citric acid, benzoic acid, ascorbic acid, etc.

When compounds of the general formula I contain chiral atoms the enantiomers, as well as mixtures thereof including the racemic mixture, belong to the invention. Pure enantiomers can be obtained by stereoselective synthesis or by resolution of the enantiomers of the end product or precursors thereof.

Compounds according to this invention can be administered either orally, locally or parenterally, in a daily dose between 0.01 and 50 mg/kg body weight, and preferably between 0.1 and 10 mg/kg body weight. For human use a daily dose between 5 and 500 mg is preferred. For this purpose the compounds are processed in a form suitable for oral, local or parenteral administration, for example a tablet, pill, capsule, solution, emulsion, paste or spray. The oral form is the most preferred form of administration.

The following examples further illustrate the preparation of the compounds used in this invention.

EXAMPLE 1

(a)

2-(5,6-Dimethoxy-benzo[b]thien-2-yl)-2-(4-morpholinyl) acetonitrile

Morpholine (10.8 ml) was added to a stirred suspension of 5,6-dimethoxy-benzo[b]thiophene-2-carboxaldehyde (5.0 g) and p-toluenesulphonic acid monohydrate (4.3 g) in dry dioxan (43 ml) under an atmosphere of nitrogen. The mixture was heated at reflux for 30 min. and then the resultant solution was cooled to 50° C. and treated in one portion with a suspension of potassium cyanide (1.46 g) in water (2.5 ml). The reaction mixture was heated at reflux for 1 hour then cooled to room temperature and treated with 15% w/v potassium carbonate in water (20 ml). The reaction mixture was then diluted with water (200 ml) and the resultant precipitate was filtered and dried to give 2-(5,6-dimethoxy-benzo[b]thien-2-yl)-2-(4-morpholinyl)acetonitrile as a pale yellow solid (6.54 g). A portion crystallized from dichloromethane/diethyl ether had m.p. 196°-199° C.

(b)

2-(5,6-Dimethoxy-benzo[b]thien-2-yl)-3-methyl-2-(4-morpholinyl) pentane dinitrile A suspension of 2-(5,6-dimethoxy-benzo[b]thiophene-2-yl)-2-(4-morpholinyl) acetonitrile in dry distilled tetrahydrofuran (70 ml) under an atmosphere of nitrogen was treated with 30% w/v potassium hydroxide in methanol (0.32 ml). A solution of crotononitrile (3.4 ml) in dry distilled tetrahydrofuran (5 ml) was then added dropwise over 10 min. After 45 min. the black solution was evaporated to dryness and the residual oil was treated with ice cold water (50 ml), the mixture was stirred, and the resultant solid was filtered and dried at 60° C. under vacuum to give 2-(5,6-dimethoxy-benzo[b]thien-2-yl)-3-methyl-2-(4-morpholinyl)pentane dinitrile as an off-white solid (7.69 g). A portion crystallized from dichloromethane/diethyl ether had m.p. 162°-165° C.

(c)

4-(5,6-Dimethoxy-benzo[b]thien-2-yl)-3-methyl-4-oxobutane nitrile.

A mixture of 2-(5,6-dimethoxy-benzo[b]thien-2-yl)-3-methyl-2-(4-morpholinyl)-pentanedinitrile (7.4 g), glacial acetic acid (37.5 ml) and water (12.5 ml) was stirred and heated at reflux under an atmosphere of nitrogen. After 45 min. the reaction mixture was cooled and poured into crushed ice (200 g). The ice was allowed to melt and the resultant precipitate was filtered and dried at 65° C. under vacuum to give 4-(5,6-dimethoxybenzo[b]thien-2-yl)-3-methyl-4-oxo-butane nitrile as a pale yellow solid (5.2 g). A portion crystallized from dichloromethane/diethyl ether had m.p. 148°-150° C.

(d)

4-(5,6-Dimethoxy-benzo[b]thien-2-yl)-3-methyl-4-oxobutanoic acid.

A mixture of 4-(5,6-dimethoxy-benzo[b]thien-2-yl)-3-methyl-4-oxo-butane nitrile (4.0 g), 1-propanol (30 ml) and 5M hydrochloric acid (28 ml) was stirred and heated at reflux for 24 hours under an atmosphere of nitrogen. The reaction mixture was cooled, diluted with water (120 ml) and the product was then extracted into ethyl acetate (2×50 ml). The organic extracts were combined, washed with water (2×20 ml), dried ($MgSO_4$), filtered, and then evaporated to give a mixture of 4-(5,6-dimethoxy-benzo[b]thien-2-yl)-3-methyl-4-oxo-butanoic acid and the corresponding propanoate ester as an oil (5.3 g). This mixture was dissolved in methanol (50 ml), then water (10 ml) and potassium carbonate (5.3 g) were added and the reaction mixture was stirred and heated at reflux. After 1 hour the solution was concentrated under reduced pressure then diluted with water (100 ml) and extracted with diethyl ether (2×30 ml). The aqueous layer was acidified with 5M hydrochloric acid and extracted with ethyl acetate (2×50 ml). The ethyl acetate extracts were combined, washed with water, dried ($MgSO_4$), filtered and evaporated to dryness to give 4-(5,6-dimethoxy-benzo[b]thien-2-yl)-3-methyl-4-oxobutanoic acid as a crystalline solid (4.2 g). A portion crystallized from diethyl ether/n-hexane had m.p. 159°-160° C.

(e)
4,5-Dihydro-6-(5,6-dimethoxy-benzo[b]thien-2-yl)-5-methyl-3(2H)-pyridazinone A mixture of 4-(5,6-dimethoxy-benzo[b]thien-2-yl)-3-methyl-4-oxo-butanoic acid (17.2 g), ethanol (356 ml) and hydrazine hydrate (85%, 55 ml) was stirred and heated at reflux. After 3 hours the reaction mixture was concentrated to about 100 ml under reduced pressure then poured into water (100 ml). The resultant solid was filtered and dried at 65° C. under vacuum to give crude pyridazinone as a white solid (15.25 g). The crude product was dissolved in hot methanol (1500 ml), filtered dust-free then concentrated and the resultant precipitate was filtered and dried to give 4,5-dihydro-6-(5,6-dimethoxy-benzo[b]thien-2-yl)-5-methyl-3(2H)-pyridazinone (14.6 g), m.p. 204°-206° C.

EXAMPLE 2

In an analogous manner as described in Example 1 were prepared:

4,5-Dihydro-6-(4-chloro-5,6-dimethoxy-benzo[b]thien-2-yl)-5-methyl-3(2H)-pyridazinone. m.p. 262°-263° C.

4,5-Dihydro-6-(5,6-dimethoxy-benzo[b]furan-2-yl)-5-methyl-3(2H)-pyridazinone. m.p. 195°-197° C.

4,5-Dihydro-6-(6-methoxy-benzo{b}thien-2-yl)-5-methyl-3(2H)-pyridazinone. m.p. 210°-212° C.

4,5-Dihydro-6-(5-hydroxy-6-methoxy-benzo[b]thien-2-yl)-5-methyl-3(2H)-pyridazinone. m.p. >275° C.

4,5-Dihydro-6-(benzo[b]thien-2-yl)-5-methyl-3(2H)-pyridazinone. m.p. 199°-200° C.

EXAMPLE 3

(a)
3-(5,6-Dimethoxy-benzo[b]thien-2-yl)-3-oxo-propanoic acid methyl ester

A mixture of sodium hydride (60% dispersion in oil, 10.9 g) and dimethyl carbonate (18.7 ml) in dry tetrahydrofuran (210 ml) was stirred and heated at reflux under an atmosphere of nitrogen. A solution of 2-acetyl-5,6-dimethoxy-benzo[b]thiophene (21.0 g) in dry tetrahydrofuran (315 ml) was added dropwise over 30 min. Shortly after the addition of the benzothiophene solution had commenced potassium hydride (22.7% dispersion in oil) was added to initiate the reaction (sufficient to cause a permanent pink colour). When the evolution of gas had ceased (90 min.) the reaction mixture was cooled in an ice bath and treated with glacial acetic acid (34 ml). The resultant yellow solution was poured into ice-cold water (2 liter), stirred, and the yellow solid was filtered, washed with n-hexane and dried at 50° C. under vacuum to give 3-(5,6-dimethoxybenzo[b]thien-2-yl)-3-oxo-propanoic acid methyl ester (22.0 g). A portion crystallized from dichloromethane/diethyl ether had m.p. 129°-130° C.

(b)
4-(5,6-Dimethoxy-benzo[b]thien-2-yl)-4-oxo-butanoic acid

Sodium hydride (60% dispersion in oil, 1.37 g) in dry tetrahydrofuran (15 ml) was stirred at room temperature under an atmosphere of nitrogen and treated dropwise over 10 min. with a solution of 3-(5,6-dimethoxybenzo[b]thien-2-yl)-3-oxo-propanoic acid methyl ester (5.0 g) in dry tetrahydrofuran (75 ml). After 30 min. ethylbromoacetate (4.0 ml) was added and the reaction mixture stirred at room temperature for a further 45 min. and then warmed to 40° C. After 2 hours the suspension was cooled, treated with glacial acetic acid (2 ml) then poured into water (400 ml). The mixture was extracted with diethyl ether (2×100 ml), the organic extracts were combined, washed with water (50 ml), dried (MgSO₄), filtered and evaporated to dryness. The residue was dissolved in ethanol (25 ml), 5M hydrochloric acid (50 ml) was added and then the solution was heated at reflux for 10 hours. The resultant white suspension was cooled to room temperature and treated dropwise with 10M potassium hydroxide (30 ml). The reaction mixture was then stirred and heated at reflux under an atmosphere of nitrogen. After 1 hour the solution was cooled, diluted with water (100 ml) and extracted with ethyl acetate (50 ml). The aqueous layer was separated, stirred and acidified with 5M hydrochloric acid (10 ml). The resultant precipitate was filtered off, washed with water and dried at 65° C. under vacuum to give 4-(5,6-dimethoxy-benzo[b]thien-2-yl)-4-oxo-butanoic acid as a pale yellow solid (4.68 g). A portion crystallized from dichloromethane/methanol had m.p. 177°-178° C.

(c)
4,5-Dihydro-6-(5,6-dimethoxy-benzo[b]thien-2-yl)-3(2H)-pyridazinone

Using the procedure described in Example 1(e), 4-(5,6-dimethoxy-benzo[b]thien-2-yl)-4-oxo-butanoic acid was converted into 4,5-dihydro-6-(5,6-dimethoxy-benzo[b]-thien-2-yl)-3(2H)-pyridazinone, m.p. 254°-256° C.

EXAMPLE 4

In an analogous manner as described in Example 3 were prepared:

4,5-Dihydro-6-(4-chloro-5,6-dimethoxy-benzo[b]thien-2-yl)-3(2H)-pyridazinone. m.p. 290°-291° C.

4,5-Dihydro-6-(5,6-dimethoxy-benzo[b]furan-2-yl)-3(2H)-pyridazinone. m.p. 188°-190° C.

EXAMPLE 5

6-(5,6-Dimethoxy-benzo[b]thien-2-yl)-3(2H)-pyridazinone

A mixture of 4,5-dihydro-6-(5,6-dimethoxy-benzo[b]-thien-2-yl)-3(2H)-pydridazinone and activated manganese dioxide (6.0 g) in dry dioxan (80 ml) and dry dimethylformamide (16 ml) was stirred and heated at reflux for 48 hours. Fresh manganese dioxide (6.0 g) was then added and the reflux was continued for a further 24 hours. The reaction mixture was then filtered through a dicalite pad and the filtrate was evaporated to dryness. The residue (1.27 g) was purified by chromatography through a column of fine silica using 3% v/v methanol/dichloromethane as the eluant. The appropriate fractions were combined, evaporated and the product was crystallized from dichloromethane/methanol to give 6-(5,6-dimethoxybenzo[b]thien-2-yl)-3(2H)-pyridazinone (0.41 g), m.p. >300° C.

EXAMPLE 6

(a)
4-(5,6-Dimethoxy-benzo[b]furan-2-yl)-4-oxo-butanoic acid methyl ester.

To a stirred suspension of 4,5-dimethoxy-2-hydroxybenzaldehyde (9.3 g) in dry ethanol (90 ml) under nitrogen was added slowly a solution of potassium hydroxide (3.14 g) in dry ethanol (60 ml). The resulting solution was stirred for 20 minutes, then 5-bromo-4-oxopentanoic acid methyl ester (10.65 g) was added slowly. The mixture was stirred for 24 hours, then diluted slowly with water (900 ml). The precipitated solid was filtered off, washed with water, dried under vacuum and crystallized from acetone-ether to give 4-(5,6-dimethoxy-benzo[b]furan-2-yl)-4-oxo-butanoic acid methyl ester (4.78 g).

A sample purified by column chromatography on silica, followed by crystallization from dichloromethane/methanol then acetone/ether had m.p. 140°–142° C.

(b) 4,5-Dihydro-6-(5 6-dimethoxy-benzo[b]-furan-2-yl)-3(2H)-pyridazinone

To a stirred suspension of 4-(5,6-dimethoxy-benzo[b]-furan-2-yl)-4-oxo-butanoic acid methyl ester (4.2 g) in ethanol (84 ml) was added water (2.1 ml), followed by reflux for 2.3/4 hours, then cooled in cold water, with water (250 ml) and acidified with 2M hydrochloric acid (150 ml). The solid was filtered off, washed with water, and dried. Purification of the crude product by column chromatography on silica and crystallization from dichloromethane/methanol gave 4,5-dihydro-6-(5,6-dimethoxy-benzo[b]furan-2-yl-3(2H)-pyridazinone (2.87 g), m.p. 188°–190° C.

EXAMPLE 7

In an analogous manner as described in Example 6 was prepared:
 4,5-Dihydro-6-(5,6-dimethoxy-benzo[b]furan-2-yl)-5-methyl-3(2H)-pyridazinone. m.p. 195°–197° C.

EXAMPLE 8

4,5-Dihydro-6-(5,6-dihydroxy-benzo[b]thien-2-yl)-5-methyl-3(2H)-pyridazinone

Boron tribromide (1.55 ml) was added to a stirred solution of 4,5-dihydro-6-(5,6-dimethoxy-benzo[b]thien-2-yl)-5-methyl-3(2H)-pyridazinone (1.14 g) in dichloromethane (200 ml). After 2 hours the orange solution was cooled in ice, and water (40 ml) was added. The dichloromethane was then evaporated off under reduced pressure and the residual suspension was filtered to give 4,5-dihydro-6-(5,6-dihydroxy-benzo[b]thien-2-yl)-5-methyl-3(2H)-pyridazinone (0.97 g) as a yellow solid. Crystallisation from dichloromethane:methanol and diethylether gave 4,5-dihydro-6-(5,6-dihydroxybenzo[b]thien-2-yl)-5-methyl-3(2H)-pyridazinone. m.p. >270° C.

EXAMPLE 9

In an analogous manner as described in Example 8 was prepared: 4,5-dihydro-6-(6-hydroxy-benzo[b]thien-2-yl)-5-methyl-3(2H)-pyridazinone. m.p. 263°–265° C.

EXAMPLE 10

4,5-Dihydro-6-(5,6-diethoxy-benzo[b]thien-2-yl)-5-methyl-3(2H)-pyridazinone

A mixture of 4,5-dihydro-6-(5,6-dihydroxy-benzo[b]thien-2-yl)-5-methyl-3(2H)-pyridazinone (1.59 g) and anhydrous potassium carbonate (1.69 g) in dimethyl formamide (18 ml) was stirred at room temperature for 10 mins. Iodoethane (0.92 ml) was then added and the reaction mixture was stirred for 16 hours. The resultant suspension was then poured into water (90 ml), the mixture was stirred, and the light yellow coloured precipitate was filtered off and dried at 75° C. under vacuum to give 4,5-dihydro-6-(5,6-diethoxy-benzo[b]thien-2-yl)-5-methyl-3(2H)-pyridazinone (1.65 g). Crystallization from dichloromethane: methanol and diethyl ether gave 4,5-dihydro-6-(5,6-diethoxybenzo[b]thien-2-yl)-5-methyl-3(2H)-pyridazinone as a white solid (1.38 g), m.p. 170°–171° C.

EXAMPLE 11

In an analogous manner as described in Example 9 were prepared:
 4,5-Dihydro-6-(6-ethoxy-benzo[b]thien-2-yl)-5-methyl-3(2H)-pyridazinone. m.p. 236°–239° C.
 4,5-Dihydro-6-(5-ethoxy-6-methoxy-benzo[b]thien-2-yl)-5-methyl-3(2H)-pyridazinone. m.p. 185°–188° C.

EXAMPLE 12

4,5-Dihydro-6-(6-methoxy-5-[3-(piperidin-1-yl)propyloxy]-benzo[b]thien-2-yl)-5-methyl-3(2H)-pyridazinone hydrochloride A mixture of 4,5-dihydro-6-(5-hydroxy-6-methoxybenzo[b]thien-2-yl)-5-methyl-3(2H)-pyridazinone (1.0 g), anhydrous potassium carbonate (1.0 g) and 1-(3-chloropropyl)piperidine hydrochloride (0.72 g) in dimethyl formamide (12 ml) was stirred at room temperature for 3 days. The mixture was then warmed to 65° C. and, after a further 2 hours, more anhydrous potassium carbonate (0.50 g) and 1-(3chloropropyl)piperidine hydrochloride (0.36 g) were added. After a further 2 hours the reaction mixture was cooled to room temperature and poured into water (60 ml). The product, which precipitated as a gum, was isolated by decantation and then crystallized from ethyl acetate to give 4,5-dihydro-6-(6-methoxy-5-[3-(piperidin-1-yl)propyloxy]-benzo[b]thien-2-yl)-5-methyl-3(2H)-pyridazinone as a white solid (0.90 g), m.p. 198°–200° C.

Conversion to hydrochloride salt: The free base (0.90 g) was suspended in methanol (50 ml) and the mixture was stirred and acidified to pH 1 using a solution of dry hydrochloric acid in methanol. The free-base dissolved and the resultant solution was filtered dust-free, concentrated and then crystallized from methanol and diethyl ether to give 4,5-dihydro-6-(6-methoxy-5-[3-(piperidin-1-yl)propyloxy]-benzo[b]thien-2-yl)-5-methyl-3(2H)-pyridazinone hydrochloride as a white solid (0.91 g). m.p. >235° C. (dec.).

EXAMPLE 13

In an analogous manner as described in Example 12, were prepared:
 4,5-Dihydro-6-(4-chloro-6-methoxy-5-[2-(piperidin-1-yl)ethyloxy]-benzo[b]thien-2-yl)-5-methyl-3(2H)-pyridazinone hydrochloride. m.p. 238°–240° C.
 4,5-Dihydro-6-(6-methoxy-5-[2-(piperidin-1-yl)ethyloxy]-benzo[b]thien-2-yl)-5-methyl-3(2H)-pyridazinone hydrochloride. m.p. 192°–200° C.
 4,5-Dihydro-6-(5-[2-(piperidin-1-yl)ethyloxy]-benzo[b]thien-2-yl)-5-methyl-3(2H)-pyridazinone hydrochloride. m.p. 245°–248° C.
 4,5-Dihydro-6-(6-[2-(piperidin-1-yl)ethyloxy]-benzo[b]thien-2-yl)-5-methyl-3(2H)-pyridazinone hydrochloride. m.p. 247°–250 1 ° C.
 4,5-Dihydro-6-(6-methoxy-5-[2-methyl-3-(piperidin-1-yl)propyloxy]-benzo[b]thien-2-yl)-5-methyl-3(2H)-pyridazinone hydrochloride.

4,5-Dihydro-6-(6-methoxy-5-[2-hydroxy-3-(piperidin-1-yl)propyloxy]-benzo[b]thien-2-yl)-5-methyl-3(2H)-pyridazinone hydrochloride.

4,5-Dihydro-6-(6-methoxy-5-[2-(4-methyl-piperazin-1-yl)ethyloxy]-benzo[b]thien-2-yl)-5-methyl-3(2H)-pyridazinone hydrochloride.

4,5-Dihydro-6-(6-methoxy-5-[2-(piperazin-1-yl)ethyloxy]-benzo[b]thien-2-yl)-5-methyl-3(2H)-pyridazinone hydrochloride.

4,5-Dihydro-6-(6-methoxy-5-[2-(morpholin-4-yl)ethyloxy]-benzo[b]thien-2-yl)-5-methyl-3(2H)-pyridazinone hydrochloride.

4,5-Dihydro-6-(5-[2-(imizadol-1-yl)ethyloxy-6-methoxy]-benzo[b]thien-2-yl)-5-methyl-3-(2H)-pyridazinone hydrochloride.

4,5-Dihydro-6-(6-methoxy-5-[2-(dimethylamino)ethyloxy]-benzo[b]thien-2-yl)-5-methyl-3-(2H)-pyridazinone hydrochloride.

4,5-Dihydro-6-(6-methoxy-5-[2-(piperidin-1-yl)ethyloxy]-benzo[b]thien-2-yl)-5-methyl-3(2H)-pyridazinone hydrochloride.

4,5-Dihydro-6-(5-[2-diethylaminoethyloxy]-6-methoxybenzo[b]thien-2-yl)-5-methyl-3(2H)-pyridazinone hydrochloride.

halogen, $NO_2$, unsubstituted or C1–C4 alkyl substituted amino, C1–C4 alkyl, C1–C4 halogen substituted alkyl, O-ALK-$NR^4R^5$, C1–C4 alkoxy, whereby two adjacent substituents taken together may also represent a methylenedioxy group;

$R^2$ and $R^3$ represent independently H or C1–C4 alkyl;

$R^4$ and $R^5$ represent independently H or C1–C4 alkyl, or form together with the nitrogen a 5- or 6- membered ring;

X represents S or O; the dotted line represents an optional bond; and their pharmaceutically acceptable salts.

2. Compounds according to claim 1, wherein $R^1$ represents OH, halogen, C1–C4 alkoxy or O-ALK-$NR^4R^5$, $R^2$ and $R^3$ represent H or $CH_3$ and there are 2, 3, or 4 substituents $R^1$, which may be the same or different.

3. Compounds according to claim 1, wherein $R^1$ represents OH, F, Cl, Br, $OCH_3$, $OC_2H_5$, 2-(piperidin-1-yl)ethyloxy or 2-(piperidin-1-yl)propyloxy, $R^2$ represents H, $R^3$ represents $CH_3$, X represents S, there are 2 or 3 substituents $R^1$ which may be the same or different and the optional bond is not present.

4. Compound according to claim 1 of the formula:

Flow sheet

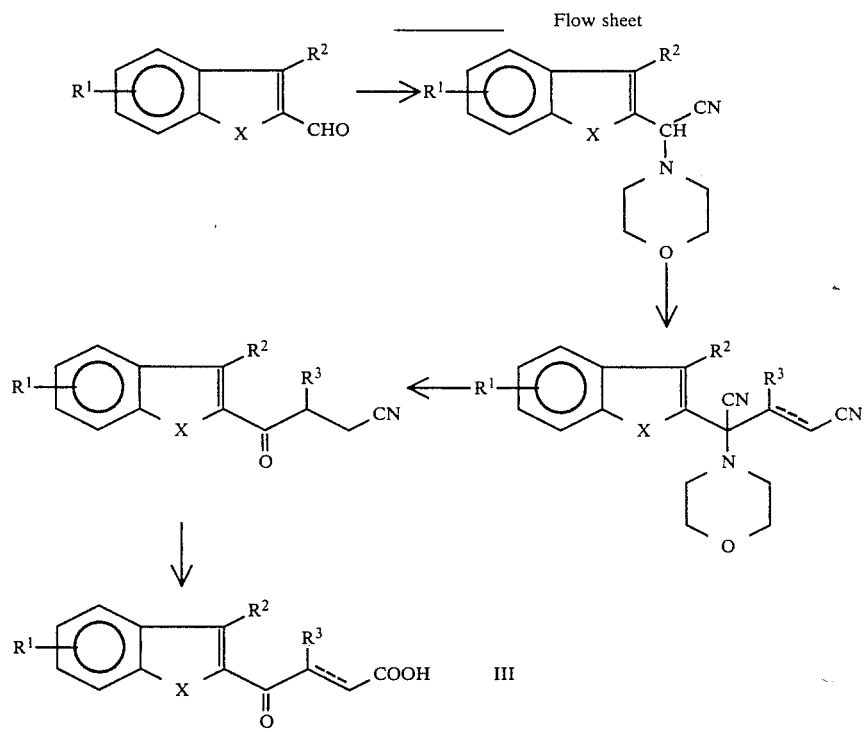

We claim:
1. Pyridazinone compounds of the formula I:

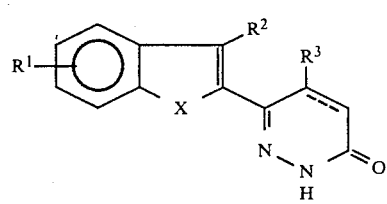

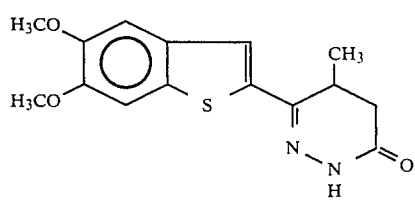

wherein
$R^1$ represents one to four substituents, which may be the same or different and are selected from H, OH, and its pharmaceutically acceptable salts.

5. Pharmaceutical preparation comprising a compound according to claim 1 in an effective amount for treating heart failure or asthma in admixture with a pharmaceutically acceptable carrier.

6. Method of treating heart failure or asthma in a patient comprising administering an effective amount of a compound according to claim 1 to achieve the effect of a pulmonary vasodilator, bronchodilator, systemic vasodilator, blood platelet aggregation inhibiting activity or cardiotonic activity.

* * * * *